United States Patent [19]
Perkins

[11] Patent Number: 5,454,782
[45] Date of Patent: Oct. 3, 1995

[54] TRANSLUMENAL CIRCUMFERENTIAL ENERGY DELIVERY DEVICE

[76] Inventor: Rodney C. Perkins, 235 Mountain Wood La., Woodside, Calif. 94062

[21] Appl. No.: 289,005

[22] Filed: Aug. 11, 1994

[51] Int. Cl.⁶ .................................................. A61B 17/36
[52] U.S. Cl. ...................................................... 604/20
[58] Field of Search ................................ 604/164, 280, 604/19–22, 53; 128/396–398; 606/39, 13–16, 45; 607/96, 113, 115, 116, 138, 156

[56] References Cited

U.S. PATENT DOCUMENTS

| | | | |
|---|---|---|---|
| 4,565,200 | 1/1986 | Cosman | 128/642 |
| 4,950,267 | 8/1990 | Ishihara et al. | 606/12 |

FOREIGN PATENT DOCUMENTS 9210142  6/1992  WIPO .

*Primary Examiner*—John D. Yasko
*Assistant Examiner*—Manuel Mendez
*Attorney, Agent, or Firm*—Haynes & Davis

[57] ABSTRACT

A probe for translumenal circumferential delivery of energy through a biological lumen comprises a catheter which is constructed and arranged to be placed within a particular biological lumen. A plurality of guide channels are formed within the catheter extending from near the proximal end to near the distal end of the catheter. The guide channels include respective diverting regions near the distal end which bend radially toward the circumference of the catheter. Energy delivery devices, such as optical fibers or electrical conductors, are placed within the guide channels and transmit energy to the distal end of the device. The energy delivery devices have relatively flexible portions near the distal ends such that when extended through the diverting region of the guide channels they are deflected radially in a direction to intersect the circumference of the biological lumen. An adaptor is coupled with the energy delivery device to supply energy for transmission to the tissue at the distal end of the device. Thus, the energy delivery device may be positioned in a withdrawn position in the catheter so that the distal end of the energy delivery device lies within the guide channel, and in an extended position so that the distal end of the energy delivery device is diverted by the diverting region of the guide channel and extends into the tissue to be treated.

18 Claims, 4 Drawing Sheets

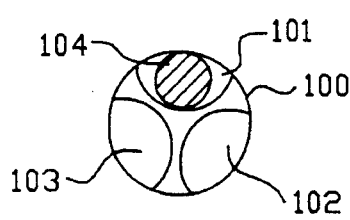
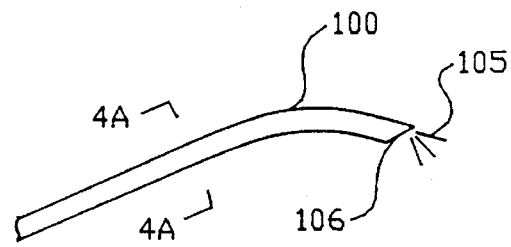
FIG.4A  FIG.4B
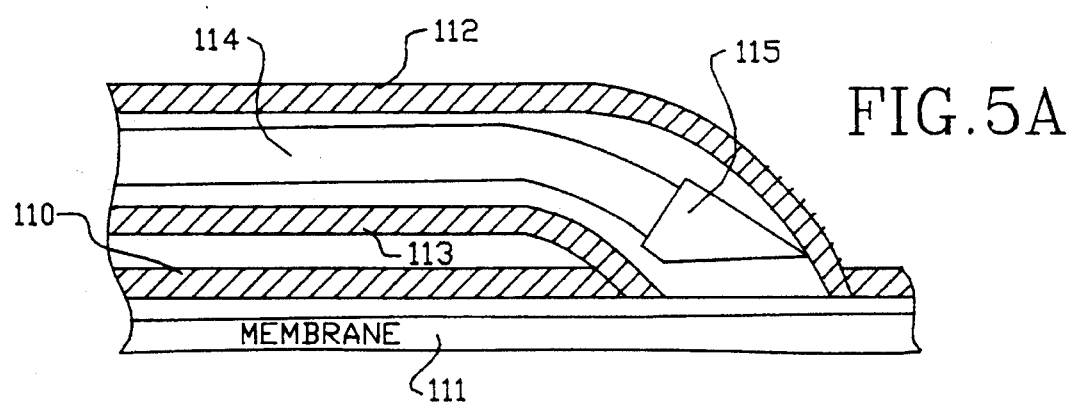
FIG.5A
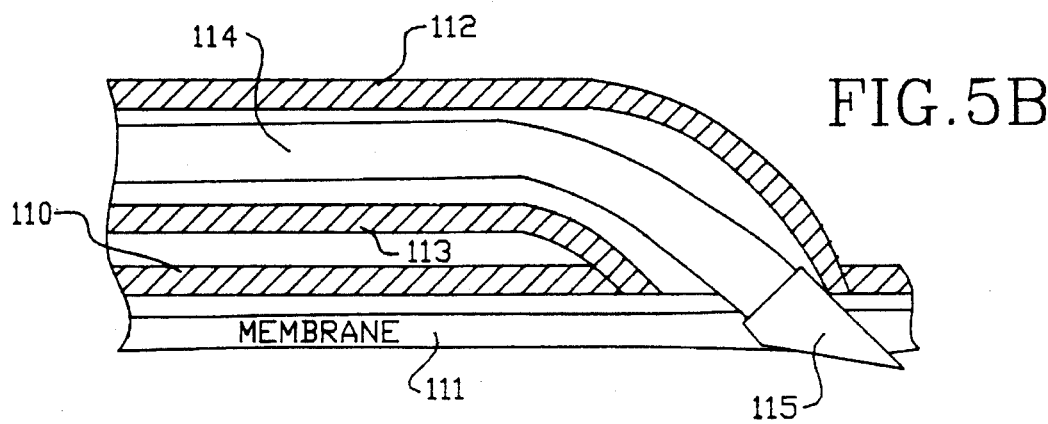
FIG.5B
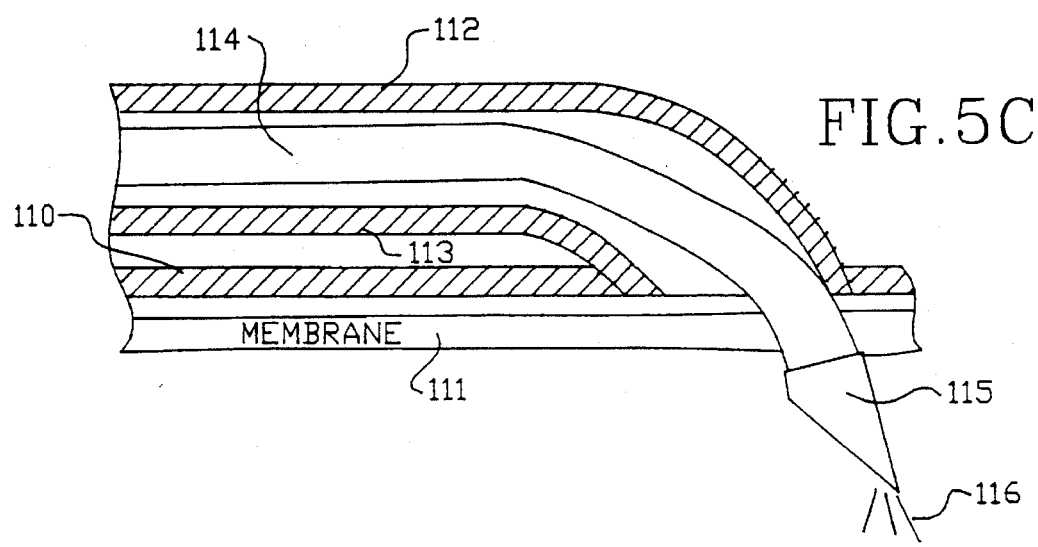
FIG.5C

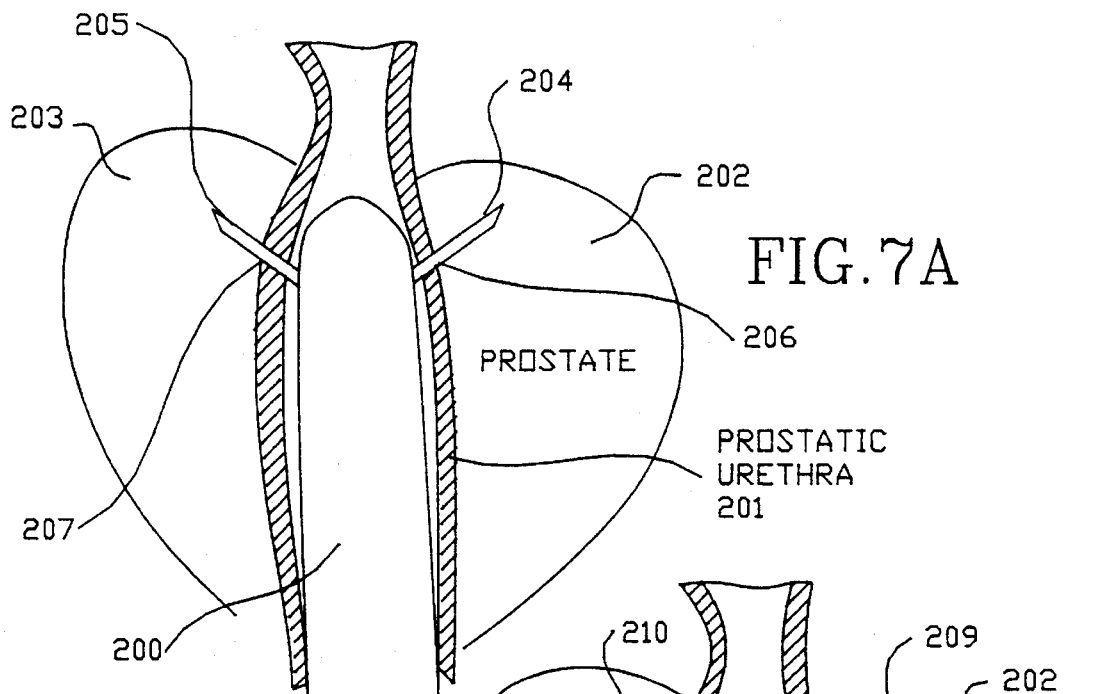
FIG. 7A
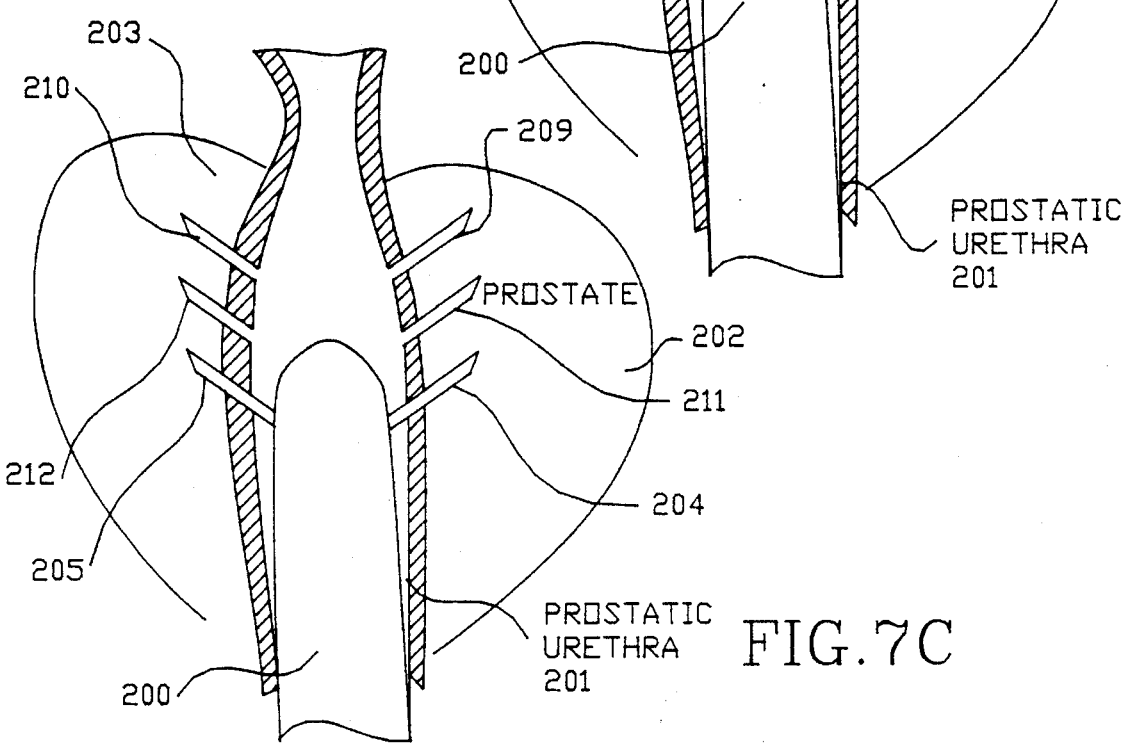
FIG. 7B
FIG. 7C 5,454,782

TRANSLUMENAL CIRCUMFERENTIAL ENERGY DELIVERY DEVICE

BACKGROUND OF THE INVENTION

Field of the Invention

The present invention relates to medical devices, and more particularly to medical devices for delivering laser output, or other types of energy, to tissues of or surrounding biological lumens such as the urethra, the esophagus, and blood vessels.

DESCRIPTION OF RELATED ART

A variety of surgical techniques have been developed which involve the delivery of energy, such as laser energy or electrical energy, by means of a catheter through a biological lumen to tissue to be treated. For instance, procedures have been developed using translumenal probes in blood vessels, the esophagus, and the urethra.

One important class of procedures being developed involves using electro-cautery or laser-induced necrosis to reduce the volume of an enlarged prostate for treatment of benign prostate hyperplasia. Generally, these techniques involve placement of a transurethral probe into the region of the prostate. A laser beam or electric current is directed laterally through the wall of the urethra to cause necrosis of the prostate tissue. The burned tissue of the prostate sloughs off over time.

Both of these techniques involved significant damage to the prostatic urethra, as the energy delivered to reduce the swollen prostate tissue must first pass through the healthy urethral wall. Thus, unnecessary damage to the healthy urethra is caused in such treatments.

Accordingly, it is desirable to provide an instrument for delivering energy to tissue surrounding a biological lumen, such as the urethra, without causing unnecessary damage to the lumen itself.

SUMMARY OF THE INVENTION

The present invention provides an apparatus for translumenal circumferential delivery of energy through a biological lumen, in which energy may be delivered directly to tissue distal to the circumference of the lumen without first passing through the lumenal wall. The apparatus comprises a catheter which is constructed and arranged to be placed within a particular biological lumen. At least one guide channel is formed within the catheter extending from near the proximal end to near the distal end of the catheter. The guide channel includes a diverting region near the distal end which bends radially toward the circumference of the catheter. An energy delivery device, such as an optical fiber or electrical conductor which transmits energy to a distal end of the device, is placed within the guide channel so that its distal end is near the distal end of the catheter. An adaptor is coupled with the energy delivery device near its proximal end to supply energy for transmission to the tissue at the distal end of the device.

The energy delivery device is pre-formed, flexible, or has a relatively flexible portion near the distal end, such that when extended through the diverting region of the guide channel it is deflected radially in a direction to intersect the circumference of the biological lumen. Thus, the energy delivery device may be positioned in a withdrawn position in the catheter so that the distal end of the energy delivery device lies within the guide channel, and in an extended position so that the distal end of the energy delivery device is diverted by the diverting region of the guide channel and extends into the tissue to be treated. The distal end of the energy delivery device may be adapted so that it pierces and extends through the wall of the biological lumen as it is moved to the extended position.

In one aspect of the invention, there are a plurality of such guide channels with corresponding energy delivery devices. The guide channels may be arranged in a radially symmetric pattern for circumferential delivery of energy to tissue surrounding a biological lumen. Other patterns of delivery can be created by alternating the position of the guide channels on the catheter.

According to another aspect of the invention, the energy delivery device is part of a treatment delivery device which includes an optical fiber or electrical conductor to transmit energy, an irrigation lumen to supply irrigation fluid to the distal end of the treatment delivery device, and an aspiration lumen to supply suction to the distal end of the treatment delivery device. The adaptor in this aspect of the invention couples energy to the optical fibers or other energy transmitting devices, couples irrigation fluid into the irrigation lumens and couples suction into the aspiration lumens.

According to yet another aspect of the invention, the probe is constructed and arranged for transurethral treatment of an enlarged prostate gland. In this aspect, the catheter is arranged so that the distal end of the treatment delivery device pierces the wall of the urethra when moved into the extended position, and reaches into the enlarged prostate gland in the extended position. Thus, laser energy or other forms of energy including but not limited to electrical, electrocautery, radio frequency and electrical magnetic emissions, may be transmitted directly into the enlarged prostate gland for resection of the diseased tissue without substantially damaging the wall of the urethra. As will be appreciated by those of skill in the art, the urethra wall may be pierced by the treatment delivery device without causing significant damage to the wall, and in a manner that the urethral wall will heal.

According to a further aspect of the invention, the probe can be used to distribute energy in a non-luminous tissue mass by penetrating it into the target tissue through a sharp catheter or needle arrangement. The sharp catheter or needle penetrates the non-luminous tissue mass, providing a path of introduction for the energy delivery device. Additionally, a trocar can be used to first penetrate the solid mass. After the trocar is removed the probe is then introduced.

The probe according to the present invention can be adapted for treatment of a variety of conditions which involve the trans-lumenal delivery of energy circumferentially to a region at or outside the wall of a biological lumen. Thus, the probe may be adapted for positioning in a blood vessel, the esophagus, the urethra, or other ducts, vessels, biological pathways or non-luminous tissues. Additionally, the probe can be used in photodynamic therapy applications.

Other aspects and advantages of the present invention can be seen upon review of the figures, the detailed description, and the claims which follow.

BRIEF DESCRIPTION OF THE FIGURES

FIG. 4A and 4B illustrate the construction of a treatment delivery device for use in the probe of FIGS. 1 and 2.

FIGS. 5A through 5C illustrate a treatment delivery device in a withdrawn position, being extended through a membrane of a biological lumen and in an extended position, respectively.

FIGS. 7A through 7C illustrate in stages one possible treatment for resection of a prostate gland using the probe of the present invention.

DETAILED DESCRIPTION

A detailed description of preferred embodiments of the present invention is provided with respect to FIGS. 1 through 7A–7C.

Figure 1:
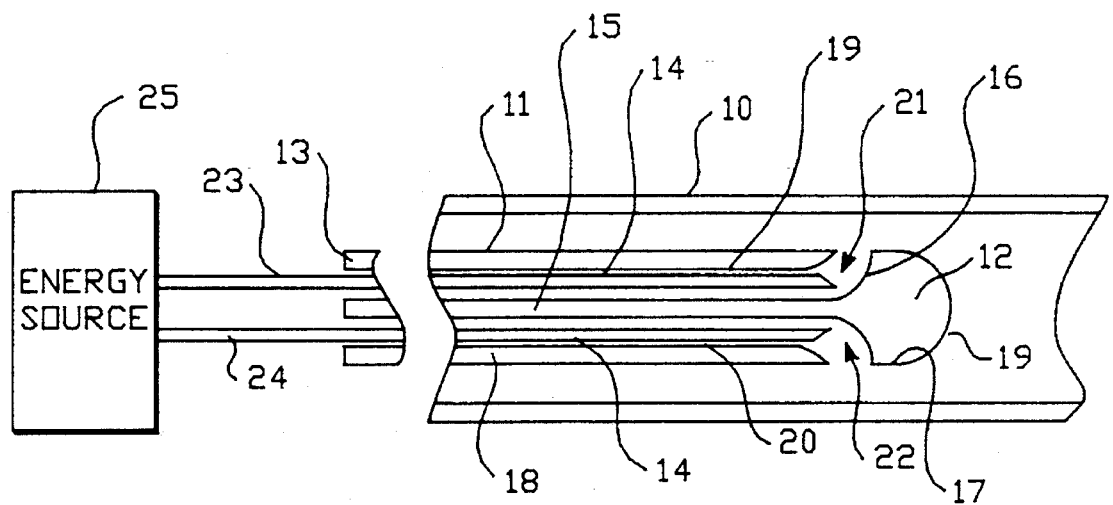
FIG. 1 is a schematic cross-sectional view of a translumenal probe according to the present invention, with energy delivery devices in the withdrawn position.

FIG. 1 is a schematic view of an apparatus for delivering energy circumferentially in a biological lumen according to the present invention. Shown in the figure is a cross-sectional view of a biological lumen 10 with probe 11 inserted therein. The probe 11 extends from a proximal end 13 to a distal end 12. Within the probe 11 are a plurality of guide channels (e.g., 14). Within probe 11, a light and/or viewing channel 15 is provided so that an operator can determine position in a lumenous structure or non-lumenous structure. Illumination and visualization elements can be provided and associated with viewing channel 15, and an optical viewing scope can be coupled with channel 15. The guide channels have a diverting region, generally 16 and 17, which bends radially toward the circumference of the lumen 10. The probe 11, according to one embodiment of the present invention, consists of a steel outer tube 18 with a closed end 19 near the distal end 12 of the probe 11. Within the outer tube 18 are a plurality of guide tubes (e.g., 19, 20) for the respective guide channels 14, 15. The tubes 19, 20 extend to and are bonded to the outer tube 18 near the distal end 12, such that the tubes 19, 20 have openings, generally 21, 22.

Flexible energy delivery devices 23, 24, such as electrical conductors or optical fibers, extend from the proximal end 13 of the probe to near the distal end 12 of the probe 11. The devices have at least a flexible portion near the distal end such that when extended through the openings 21, 22, the devices bend radially toward the circumference of the lumen 10.

The devices 23, 24 are coupled with an adaptor (not shown) to an energy source 25, such as a laser, electrical power supply, electrocautery, radio frequency or magnetic emissions device. As described below, irrigation and aspiration sources may also be coupled to the devices.

FIG. 1 illustrates the devices 23, 24 in a withdrawn position, such that the distal ends do not extend out openings 21, 22. The probe 11 is positioned within the lumen 10 using techniques known in the art. For instance, for a transurethral probe, a sheath with an obturator may be positioned within the urethra. The obturator is removed, and the probe 11 is inserted through the sheath in place of the obturator. Rectal ultrasound, or other monitoring techniques, may be used to precisely position the distal end 12 of the probe 11 within the urethra prior to extending the devices, and delivering the energy. Alternatively, position can be determined visually through viewing channel 15 with an endoscope associated therein.

Figure 2:
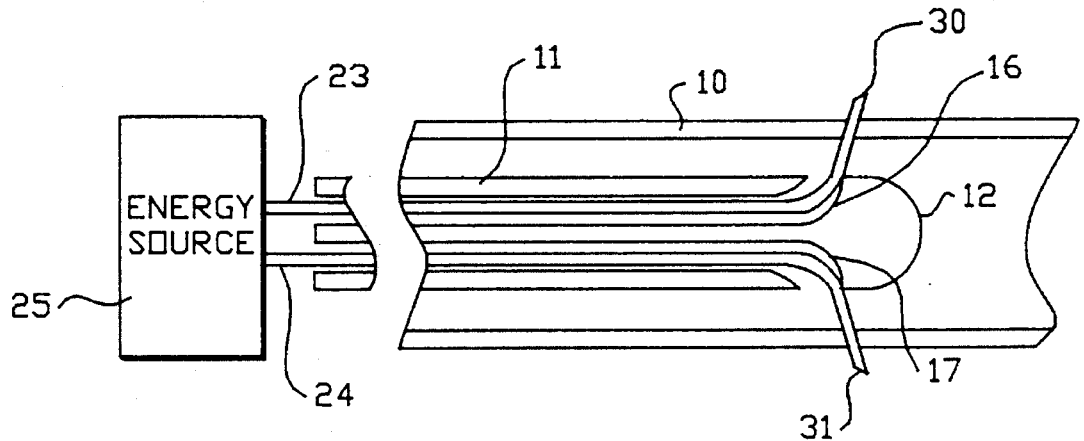
FIG. 2 is a schematic cross-sectional view of the translumenal probe of the present invention with the energy delivery devices in an extended position.

FIG. 2 illustrates the probe of FIG. 1, with the devices 23, 24 in an extended position. The reference numbers in FIG. 2 are the same as the reference numbers in FIG. 1 for like elements. After the distal end 12 of the probe 11 is positioned within the lumen 10, the devices 23 and 24 are driven longitudinally in the direction of the distal end 22, as schematically illustrated in FIG. 2 by the position of the energy source 25 relative to the position of the same in FIG. 1. By forcing the devices 23, 24 to the extended positions, the diverting regions 16, 17 of the guide channels 14, 15 deflect the distal ends 30, 31 toward the circumference of the lumen 10. As illustrated in FIG. 2, the devices may be extended radially through the wall of the lumen 10 to deliver energy outside the wall 10. Thus, it can be seen that the devices 23, 24 have a withdrawn position (FIG. 1), in which the tips 30 and 31 are within the guide channels, and an extended position (FIG. 2) in which the tips 30 and 31 extend to or through the wall of the lumen 10.

The probe 11 according to FIGS. 1 and 2 may be manufactured using a variety of materials, including plastic, steel, or aluminum. The probe 11 may also be manufactured using a flexible material such as plastic, adapted for use in smaller vessels as known in the catheter materials art.

The energy delivery device may comprise an electrical conductor which would consist of a wire coated with an insulating material and having a beveled tip. In this way, the tips 30, 31 are adapted to pierce the wall 10 of the lumen. Alternatively, the energy delivery device comprise an optical fiber with a bevelled or tapered tip to facilitate piercing the wall 10 of the lumen. The fibers may be equipped in another embodiment with an attached tip as illustrated in FIGS. 5A–5C and described in more detail below.

Further, the energy delivery device may be configured as part of a more complex treatment delivery device which includes lumens not only for the delivery of energy such as through an optical fiber, but also lumens for supplying irrigation fluid and suction to the distal end of the device for use in conjunction with the energy treatment. Thus, if the laser energy is used to evaporate tissue, the aspiration lumen may withdraw the generated smoke. Irrigation fluid may be used in conjunction with the suction provided through the aspiration lumen to clean the tip of the energy delivery device, or flush the region being treated of blood and debris. Furthermore, an optical fiber lens may be included in the device to provide direct visualization for some treatment methods.

Figure 3:
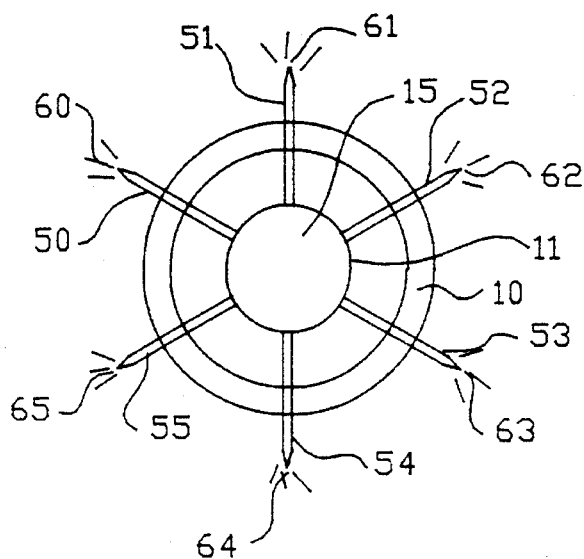
FIG. 3 is a schematic end view of the translumenal probe illustrating a radially symmetric implementation.

FIG. 3 provides an end view of the probe 11 within lumen 10. In FIG. 3, the probe is equipped with six energy delivery devices 50, 51, 52, 53, 54, and 55, which in this case are optical fibers. The six optical fibers 50–55 are arranged in a radially symmetric pattern about the probe 11, and extend through the wall of the lumen 10 to deliver energy generally through tapered tips 60, 61, 62, 63, 64, and 65.

The tapered tips may be used to concentrate the laser energy delivered by the fibers, as well as facilitate piercing the wall of the lumen with the optical fibers.

The use of a plurality of optical fibers in a single probe allows the designer to construct and arrange the probe with a specific pattern for efficiency of a particular treatment. Thus, non-symmetric patterns may be useful for tissue which is not arranged completely around the lumen, or for other reasons.

FIGS. 4A and 4B illustrate the structure of a treatment delivery device according to one embodiment of the present invention. FIG. 4A illustrates a cross-section of a flexible catheter 100 which is manufactured using extruded plastic material. The catheter includes a first lumen 101, a second lumen 102, and a third lumen 103. An optical fiber 104 is positioned within the first lumen 101. FIG. 4B illustrates a side view of the multilumen device 100 in which the cross-sectional view of FIG. 4A may be considered as having been taken at lines 4A–4A. FIG. 4B illustrates that the catheter 100 is generally flexible and provides for the delivery of energy, generally 105, out the distal end of the probe. Also, the device tip 106 may be cut angularly to facilitate piercing the tissue in a biological lumen. The multi-lumen device 100 may be normally straight, or be constructed of a pre-formed flexible material which normally has a bend in it, unless withdrawn within the guide channel.

FIGS. 5A–5C illustrate the use of a treatment delivery device with a diverting probe according to the present invention to pierce the membrane of a biological lumen. Thus, FIG. 5A illustrates a partial cross-section of a probe according to the present invention. The outside wall 110 of the probe extends essentially parallel to a membrane 111 of a biological lumen. A guide channel having a first side 112 and a second side 113 is illustrated. A treatment delivery device 114, such as that illustrated with respect to FIGS. 4A and 4B is positioned between the walls 112, 113 of the guide channel. In this embodiment, the treatment delivery device 114 is equipped with a tip 115 designed to facilitate piercing the membrane 111, without fouling the end of the catheter acting as the treatment delivery device 114.

The tip 115 may be bonded to the catheter 114 using surgical grade adhesive, or a combination of adhesive and mechanical techniques well known in the catheter arts. The material of the tip 115 may comprise hard plastic, aluminum, steel, quartz, or other materials as suits the needs of a particular application.

In FIG. 5A, the treatment delivery device 114 is illustrated in a withdrawn position. In FIG. 5B, the treatment delivery device 114 is illustrated in a partially extended position, which pierces the membrane 111 by a mechanical action of the tip 115.

In FIG. 5C, the same mechanism is illustrated in a fully extended position in which the tip 115 is extended completely through the membrane 111. In this position, laser energy, generally 116, is supplied through the optical fiber within the treatment delivery device 114 into the tissue outside the membrane 111.

The laser energy 116 delivered by the mechanism may be adapted to any of a variety of uses. For instance, it may be used to evaporate tissue, to cause necrosis, or to illuminate photoactive dyes, such as used in photodynamic therapy.

Thus, with reference to FIGS. 5A—5C, one can see that the translumenal circumferential delivery of energy is accomplished without damage to the membrane 111 of the lumen, except as caused by the mechanical piercing of the membrane by the treatment delivery device 114. Alternatively, energy may be applied to evaporate a small hole in the lumenal wall, or a combination of energy and mechanical pressure may be used.

Figure 6:
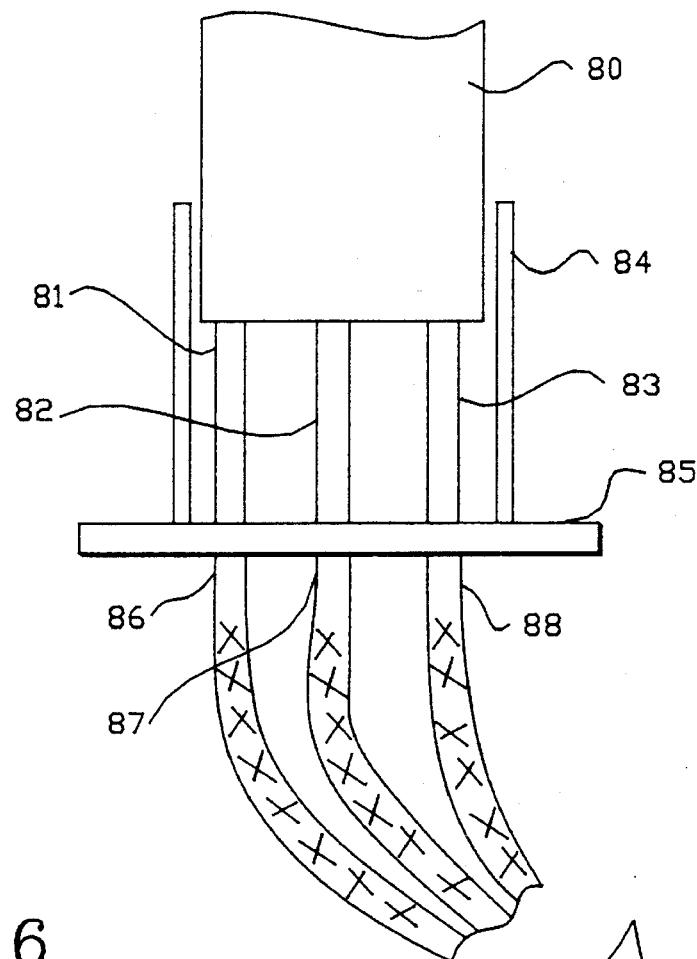
FIG. 6 is a schematic illustration of a system for delivering energy, irrigation and aspiration to a probe according to the present invention.
Figure 6:
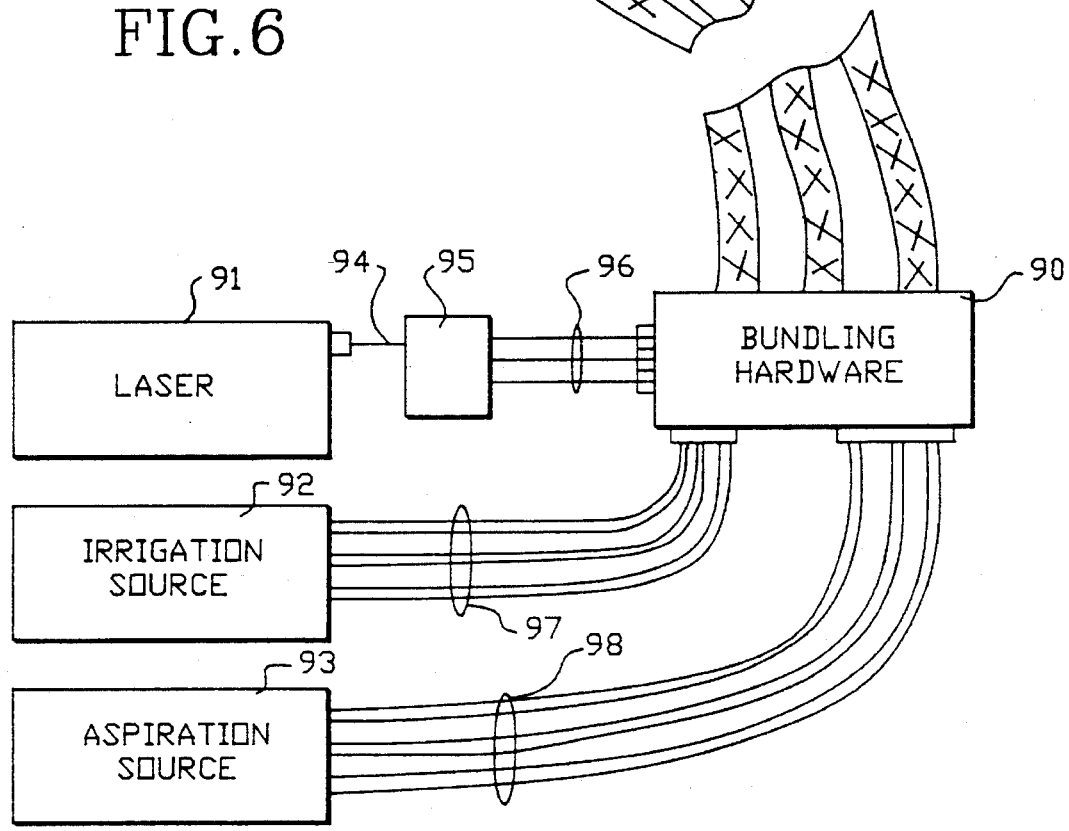

In FIG. 6, the proximal end of a probe 80 according to the present invention is illustrated. Treatment delivery catheters 81, 82, and 83 extend out of the proximal end of the probe 80, and as appreciated with reference to FIGS. 1 and 2, through guide channels down the length of the probe 80. The probe 80 is secured to a sheath 84. The sheath 84 is connected with plate 85.

The catheters 81, 82, 83 are secured to the plate 85 and pass through as bundles 86, 87, and 88. The bundles 86, 87, and 88 are flexible members coupled to a bundling mechanism, generally 90. The bundling mechanism supplies the energy, in this case laser energy, for transmission down the respective bundles 86, 87, 88 through catheters 81, 82, 83 to the distal end of the probe. In addition, irrigation fluid and suction for aspiration are provided into the bundles 86, 87, and 88 for transmission down to the distal end of the probe. Thus, the device 90 consists mainly of plumbing and connectors needed to accomplish this bundling of energy, irrigation, and aspiration delivery mechanisms. The bundling mechanism 90 may be implemented using a wide variety of techniques known in the art.

The inputs to the bundling mechanism are supplied from a laser 91, an irrigation source 92, and an aspiration source 93. For the embodiment having three bundles, 86, 87, and 88, the output of the laser supplied on optic 94 to a beam splitting mechanism 95 which splits the beam and couples it into a set of three fibers, generally 96, into the coupling mechanism 90. The fibers 96 are then coupled into the bundles 86, 87, and 88 as known in the art for delivery of energy.

The output of the irrigation source 92 includes a bundle of tubes, generally 97, having one irrigation channel per bundle 86, 87, 88. Similarly, the aspiration source supplies suction to a bundle of tubes, generally 98, including one tube for each bundle 86, 87, 88.

Thus, the bundling hardware 90 receives laser energy through fiber optics 96, irrigation fluid through tubes 97, and suction for aspiration through tubes 98, and bundles the tubing or fiber optics into flexible bundles 86, 87, 88 which are coupled to the catheters 81, 82, and 83 of the probe.

In operation, the probe 80 is placed within the lumen subject of treatment. The plate 85 is then driven toward the probe 80, with alignment and protection of the structure of the catheters 81, 82, and 83 provided by the sheath 84. The flexible bundles 86, 87, and 88 allow for the range of motion of the plate 85 required for withdrawing or extending the catheters through the probe 80. Also, the plate 85 may provide a stop mechanism, which prevents over-extension of the catheters out of the probe 80.

FIGS. 7A–7C illustrate a treatment procedure using the probe according to the present invention for transurethral resection of an enlarged prostate gland. Thus, as can be seen in FIG. 7A, a probe 200 according to the present invention is placed within the urethra. The figure illustrates the prostatic urethra 201, which consists of the wall of the lumen in the region of the prostate. The prostate gland, as illustrated in FIG. 7A, includes lobes 202 and 203 which surround the prostatic urethra 201. After positioning the probe 200, the treatment delivery devices 204 and 205 are driven into the extended position, piercing the prostatic urethra at positions 206 and 207. After extending through the prostatic urethra 201, laser energy may be delivered through the devices at a wavelength selected to evaporate the tissue along the channel created by the physical positioning of the device 204, 205. Laser energy may be delivered at a first wavelength such as 532 nanometers to evaporate the tissue during a first part of the procedure, and then switched to a second wavelength such as 1064 nanometers to cause necrosis of surrounding tissue to increase the volume of tissue being destroyed in the treatment procedure.

After the delivery of energy at the position illustrated in

FIG. 7A, the treatment devices 204 and 205 are withdrawn, and the probe 200 repositioned as illustrated in FIG. 7B. As can be seen in FIG. 7B, regions 209 and 210 are left in the prostate lobes 202 and 203, which reduce the interstitial pressure of the tissue in the gland. Also, at the new position, as illustrated in FIG. 7B, the energy delivery devices 204 and 205 may be reextended and the treatment repeated.

FIG. 7C illustrates that after withdrawal of the devices 204 and 205 when in the position of FIG. 7B, the probe 200 may be repositioned for a third treatment. Thus, it can be seen that regions 209 and 210 from the first treatment cycle of FIG. 7A and regions 211 and 212 from the second treatment cycle of FIG. 7B are treated, and new regions as illustrated by the positions of the treatment delivery devices 204 and 205 will be treated after the third cycle of FIG. 7C.

This procedure may be repeated a number of times using precise positioning techniques, such as rectal ultrasound, or the like. Of course, the sequence of FIGS. 7A–7C is a simplified depiction of the procedure. A variety of optimized and precise positioning techniques may be used according to a specific application or condition of the patient to be treated.

A significant amount of prostate tissue may be removed, and interstitial pressure of the gland reduced without causing widespread damage to the prostatic urethra 201. Rather, the urethra is pierced by the devices 204 and 205, causing relatively small amount of damage which heals readily. The amount of damage overall to the prostatic urethra 201 in this procedure is significantly reduced over prior art transurethral systems for resection of the prostate using electrocautery or laser induced necrosis of the prostate tissue.

The dimensions of the mechanism can be very small as suits the needs of the particular procedure. For instance, an optical fiber having a 400 micron outside diameter may be used, such that the overall outside diameter of a probe carrying three such fibers may be on the order of 1 or 2 millimeters. For biological lumens, such as the urethra, which support a larger probe, the overall outside diameter of the probe carrying from three to six treatment delivery devices one or two millimeters in diameter each, may be on the order of a centimeter.

The treatment delivery devices of the present invention can be used in a variety of structures including but not limited to the esophagus, laerimal ducts, salivary ducts, lute ducts and non-lumenous masses. With a solid mass an instrument such as a trocar can be used to penetrate the mass. The trocar is then removed, probe introduced, and the energy delivery devices can then deliver a desired type and amount of energy throughout the mass.

Although not shown in the figures, the treatment delivery devices may be fitted with viewing optics associated with viewing channel 15 in addition to the energy transmitting optic, the irrigation and the aspiration lumens. Further, the probe 12 of FIGS. 1 and 2 may be adapted to include a viewing scope along the axis of the device in addition to the guide channels.

In sum, a mechanism for translumenal circumferential delivery of energy for treatment of tissue of or surrounding biological lumens has been provided. The device provides for the delivery of energy without causing significant damage to the wall of the lumen, it therefore eases recovery of the patient from such procedures.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

I claim:

1. An apparatus for translumenal delivery of energy through a biological lumen having a circumference, comprising:

a catheter having a proximal end and a distal end to position within a biological lumen;

at least three guide channels forming a plurality of guide channels within the catheter and positioned about the circumference of the catheter, the plurality of guide channels extending from near the proximal end to near the distal end of the catheter, each guide channel including a diverting region near the distal end bending radially;

a plurality of energy delivery devices within corresponding guide channels in the plurality of guide channels, the plurality of energy delivery devices having distal ends, wherein the plurality of energy delivery devices within the plurality of guide channels may be positioned in a withdrawn position so that the distal ends of the plurality of energy delivery devices lie within the guide channels, and in an extended position so that the distal ends of the plurality of energy delivery devices are diverted by the diverting regions of the guide channels and extend circumferentially about the circumference of the catheter; and an adaptor, coupled with the plurality of energy delivery devices, to supply energy for transmission through the plurality of energy delivery devices.

2. The apparatus of claim 1, wherein the diverting regions of the plurality of guide channels establish a substantially radially symmetrical pattern.

3. The apparatus of claim 1, further including:

an energy source coupled to the adaptor.

4. The apparatus of claim 1, wherein the biological lumen has a wall at the circumference, and the plurality of energy delivery devices extend circumferentially through the wall in the extended position.

5. The apparatus of claim 1, wherein the catheter comprises a transurethral probe.

6. The apparatus of claim 1, wherein the catheter comprises a probe adapted for translumenal positioning in an esophagus.

7. The apparatus of claim 1, wherein the catheter comprises a probe adapted for translumenal positioning in a blood vessel.

8. The apparatus of claim 1, wherein the catheter comprises a probe adapted for translumenal positioning in a laerimal duct.

9. The apparatus of claim 1 wherein the catheter comprises a probe adapted for translumenal positioning in a salivory duct.

10. The apparatus of claim 1, wherein the catheter comprises a probe adapted for translumenal positioning in a bile duct.

11. The apparatus of claim 1, wherein the catheter comprises a probe adapted for positioning in a nonlumenous mass.

12. The apparatus of claim 1, wherein the plurality of energy delivery devices comprise wave guides for transmission of electromagnetic energy.

13. The apparatus of claim 1, wherein the plurality of energy delivery devices comprise fiber optics for transmission of laser energy.

14. The apparatus of claim 1, wherein the plurality of energy delivery devices comprise conductors for transmission of electrical energy.

15. A translumenal probe for laser treatment of tissue in a region near a biological lumen, the biological lumen having a circumference near the tissue to be treated, comprising:

a catheter having a proximal end and a distal end to position within the biological lumen;

at least three guide channels forming a plurality of guide channels within the catheter and positioned about the circumference of the catheter, the plurality of guide channels extending from near the proximal end to near the distal end of the catheter, the guide channels including respective diverting regions near the distal ends bending radially;

a plurality of treatment delivery devices within corresponding guide channels in the plurality of guide channels, the treatment delivery devices having respective distal ends, wherein the plurality of treatment delivery devices may be positioned in a withdrawn position so that the distal ends of the treatment delivery devices lie within the guide channels, and in an extended position so that the distal ends of the treatment delivery devices are diverted by the diverting regions of the guide channels and extend circumferentially about the circumference of the catheter to the tissue to be treated, each of the treatment delivery devices including an optical fiber to transmit electromagnetic energy to the distal end of the treatment delivery device, an irrigation lumen to supply irrigation fluid to the distal end of the treatment delivery device and an aspiration lumen to supply suction to the distal end of the treatment delivery device; and an adaptor, coupled with the plurality of treatment delivery devices, to couple electromagnetic energy to the optical fibers, irrigation fluid to the irrigation lumens and suction to the aspiration lumens.

16. The translumenal probe of claim 15, wherein the diverting regions in the plurality of guide channels tend to divert the plurality of treatment delivery devices circumferentially in a radially symmetrical pattern.

17. The translumenal probe of claim 15, wherein the catheter is constructed and arranged for transurethral treatment of an enlarged prostate gland.

18. The translumenal probe of claim 17, wherein the biological lumen is a urethra having a wall, and the catheter is constructed and arranged so that the distal ends of the plurality of treatment delivery devices pierce the wall of the urethra when being moved to the extended position, and reach into the enlarged prostate gland in the extended position, so that the electromagnetic energy is transmitted to the enlarged prostate gland though the plurality of treatment delivery devices without substantially damaging the wall of the urethra.

* * * * *